US007019109B2

(12) United States Patent
Rivier et al.

(10) Patent No.: US 7,019,109 B2
(45) Date of Patent: Mar. 28, 2006

(54) SSTR1-SELECTIVE ANALOGS

(75) Inventors: Jean E. F. Rivier, La Jolla, CA (US); Jean Claude Reubi, Berne (CH)

(73) Assignee: The Salk Institute for Bilogical Studies, La Jolla, CA (US)

( * ) Notice: Subject to any disclaimer, the term of this patent is extended or adjusted under 35 U.S.C. 154(b) by 441 days.

(21) Appl. No.: 10/099,240

(22) Filed: Mar. 15, 2002

(65) Prior Publication Data
US 2002/0173618 A1   Nov. 21, 2002

Related U.S. Application Data

(60) Provisional application No. 60/276,871, filed on Mar. 16, 2001.

(51) Int. Cl.
C07K 7/665     (2006.01)
C07K 7/64      (2006.01)

(52) U.S. Cl. .................. 530/311; 530/300; 530/317

(58) Field of Classification Search ............ 530/300, 530/311, 317; 514/2
See application file for complete search history.

(56) References Cited

U.S. PATENT DOCUMENTS

| 5,597,894 | A | 1/1997 | Coy et al. |
| 5,750,499 | A | 5/1998 | Hoeger et al. |
| 5,932,189 | A | 8/1999 | Dean et al. |
| 5,955,426 | A | 9/1999 | Dean et al. |
| 5,962,409 | A | 10/1999 | Deghenghi |
| 5,972,308 | A | 10/1999 | Dean |
| 5,976,496 | A | 11/1999 | Dean et al. |
| 6,001,801 | A | 12/1999 | Coy et al. |
| 6,579,967 | B1 * | 6/2003 | Rivier et al. ............. 530/311 |
| 2003/0119021 | A1 * | 6/2003 | Koster et al. ............. 435/6 |

OTHER PUBLICATIONS

JC Reubi, et al. A selective analog for the somatostatin sst1-receptor subtype expressed by human tumors (1998) European Journal of Pharmacology. 345, 103-110.*

L Chen, et al., Structural basis for the binding specificity of a SSTR1-selective analog of somatostatin (1999) Biochemical and Biophysical Research Communications, 258, 689-694.*

G Liapakis, et al. Development of a selective agonist at the somatostatin receptor subtype SSTR1 (1996) Journal of Pharmacology and Experimental Therapeutics, 276, 1089-1094.*

KH Jorgensen and UD Larsen. Homogeneous mono (125) l-insulins. Preparation and characterization of mono-(125) l-(tyr a14)- and mono-(125)l-(tyr a19)- insulin (1980) Diabetologia, 19, 546-554, Abstract Only.*

Curtis et al., Somatostatin receptor subtype expression and function in human vascular tissue, *Am. J. Physiol. Heart Circ. Physiol.*, 278: pp. H1815-H1822 (2000).

De Jong et al., Pre-Clinical Comparison of [DTPA$^0$] Octreotide, [DTPA$^0$, Tyr$^3$] Octreotide and [DOTA$^0$, Tyr$^3$] Octreotide as Carriers for Somatostatin Receptor-Targeted Scintigraphy and Radionuclide Therapy, *Int. J. Cancer*: 75, 406-411 (1998).

* cited by examiner

*Primary Examiner*—Christopher R. Tate
*Assistant Examiner*—Andrew D. Kosar
(74) *Attorney, Agent, or Firm*—Fitch, Even, Tabin & Flannery

(57) ABSTRACT

Analogs of SRIF which are selective for SSTR1 in contrast to the other cloned SRIF receptors. These analogs are useful in determining the tissue and cellular expression of the receptor SSTR1 and its biological role in the endocrine, exocrine and nervous system, as well as in regulating tumor growth. SRIF analog peptides, such as des-AA$^{1,2,5}$[D-Trp$^8$, N$^\alpha$MeIAmp$^9$, Tyr$^{11}$]-SRIF and counterparts incorporating Cbm at the N-terminus and/or N$^\alpha$Ser$^{13}$, inhibit the binding of a universal SRIF radioligand to the cloned human receptor SSTR1, but they do not bind with significant affinity to human SSTR2, SSTR3, SSTR4 or SSTR5. By incorporating an iodinated tyrosine in position-2 or in position-11 in these SSTR1-selective SRIF analogs, a labeled compound useful in drug-screening methods is provided. The N-terminus accommodates bulky moieties without loss of selectivity, and a carbamoyl moiety or a conjugating agent that will accept a radioactive nuclide or will link to a cytotoxin may be present at the N-terminus.

20 Claims, No Drawings

SSTR1-SELECTIVE ANALOGS

This application claims priority from U.S. Ser. No. 60/276,871, filed Mar. 16, 2001, the subject matter of which is incorporated herein by reference.

This invention was made with Government support under Grant No. 5R01 DK50124 awarded by the National Institutes of Health. The Government has certain rights in this invention.

This invention is directed to peptides related to somatostatin and to methods for pharmaceutical treatment of mammals using such peptides. More specifically, the invention relates to shortened receptor-selective somatostatin analogs and the inclusion of amino acid substitutions in such analogs and optional modification of the N-terminus that confer thereto receptor-selectivity and/or increased affinity to the recetor, to pharmaceutical compositions containing such peptides, to such peptides complexed with radioactive nuclides or conjugated to cytotoxins, to methods of diagnostic and therapeutic treatment of mammals using such peptides and their conjugates, particularly peptides that are chelated or otherwise labelled, and to methods for screening for more effective drugs using such peptides.

BACKGROUND OF THE INVENTION

The cyclic tetradecapeptide somatostatin-14 (SRIF) was originally isolated from the hypothalamus and characterized as a physiological inhibitor of growth hormone release from the anterior pituitary. SRIF is localized throughout the central nervous system, where it acts as a neurotransmitter and has been shown to both positively and negatively regulate neuronal firing, to affect the release of other neurotransmitters, and to modulate motor activity and cognitive processes.

Somatostatin and many analogs of somatostatin exhibit activity in respect to the inhibition of growth hormone (GH) secretion from cultured, dispersed rat anterior pituitary cells in vitro; they also inhibit GH, insulin and glucagon secretion in vivo in the rat and in other mammals. One such analog is [D-Trp$^8$]-SRIF which has the amino acid sequence: (cyclo 3-14)H-Ala-Gly-Cys-Lys-Asn-Phe-Phe-D-Trp-Lys-Thr-Phe-Thr-Ser-Cys-OH, which is disclosed in U.S. Pat. No. 4,372,884 (Feb. 8, 1983). Somatostatin has also been found to inhibit the secretion of gastrin and secretin by acting directly upon the secretory elements of the stomach and pancreas, respectively, and somatostatin is being sold commercially in Europe for the treatment of ulcer patients. SRIF is also known to inhibit the growth of certain tumors.

SRIF induces its biological effects by interacting with a family of membrane-bound structurally similar receptors. Five SRIF receptors have been cloned and are referred to as SSTR1–5. All five receptors bind SRIF and SRIF-28 (an N-terminally extended version) with high affinity; however, studies have now shown that different receptor subtypes mediate distinct functions of SRIF in the body.

A cyclic SRIF analog, variously termed SMS-201-995 and Octreotide, i.e. D-Phe-c[Cys-Phe-D-Trp-Lys-Thr-Cys]-Thr-ol is being used clinically to inhibit certain tumor growth; analogs complexed with $^{111}$In or the like are also used as diagnostic agents to detect SRIF receptors expressed in cancers. Two similar octapeptide analogs having 6-membered rings, i.e. Lanreotide and Vapreotide, have also been developed, see Smith-Jones et al., *Endocrinology*, 140, 5136–5148 (1999). A number of versions of these somatostatin analogs have been developed for use in radioimaging or as radiopharmaceuticals in radionuclide therapy; for radioimaging, for example, labeling with $^{125}$I can be used. Proteins have been previously radiolabeled through the use of chelating agents, and there are various examples of complexing somatostatin analogs with $^{99}$Tc, $^{90}$Y or $^{111}$In. A variety of complexing agents have been used including DTPA (Virgolini, et al., *European Journal of Nuclear Medicine*, 23:1388–1399, October 1996); (Stabin, et al., *J. Nuc. Med.*, 38:1919–1922, December 1997); (Vallabhajosula, et al., *J. Nuc. Med.*, 37:1016–1022, June 1996); DOTA (De Jong, et al., *Int. J. Cancer*, 75:406–411, 1998); (Froidevaux, et al., *Peptide Science-Present and Future*, 670–673, 1999); HYNIC (Decristoforo, et al. *Eur. J. Nuc. Med.*, 26:869–876); (Krois, et al., *Liebigs Ann.*, 1463–1469, 1996); and P$_2$S$_2$-COOH (Karra, et al., *Bioconjugate Chem.*, 10:254–260, 1999. Another such complexing/conjugating agent sometimes used is succinimidyl 6-hydrazinium nicotinate hydrochloride (SHNH). A wide variety of such complexing/conjugating agents are disclosed and discussed in U.S. Pat. No. 5,972,308 (Oct. 26, 1999).

Interventional treatment to the arterial system, such as angioplasty or bypass surgery, can be damaging to the vessel wall. Injuries to the vessel wall lead to a complex cascade of reparative responses starting with mural thrombi formation. Death of medial smooth muscle cells (SMC) from vessel wall injury also initiates the release of growth factors, such as basic fibroblast growth factor (bFGF) and platelet-derived growth factor from platelets, macrophages, and endothelial cells. These factors subsequently stimulate the proliferation and migration of medial SMC into the intima. Prolifering SMC synthesize and secrete a wide variety of mitogenic growth factors to promote further SMC proliferation and elaboration of extracellular matrix. This reparative process terminates when the damaged endothelium has been restored. However, if cell proliferation and matrix deposition continue, they lead to a pathological condition known as intimal hyperplasia (IH).

Clinically, IH causes renarrowing, or restenosis, of treated arteries in 30–50% of coronary angioplasties within six months and in ~20% of bypass procedures within two years after treatment. Apart from intravascular stents and anticoagulation, which appear effective in limiting restenosis in the short term, no other interventions have been successful in halting the development of IH; however, there is now evidence that SRIF may have an effect upon IH.

Recent evidence indicates that a somatostatin (SRIF) analog, angiopeptin (BIM-23014), is effective in inhibiting IH after arterial injury in animal models. Angiopeptin inhibits the release of insulin-like growth factor-1 and bFGF from endothelial cells, thus preventing SMC proliferation and migration. Clinical trials using angiopeptin to inhibit IH-causing restenosis, however, have been inconclusive. Angiopeptin is selective for SSTR2, SSTR3 and SSTR5, and IH appears to be mediated by SSTR1, which may explain the inconclusive results.

Octreotide, angiopeptin and other clinically used SRIF analogs interact significantly with three of the receptor subtypes, i.e. SSTR2, SSTR3 and SSTR5. SSTR2 and SSTR5 have recently been reported to mediate antiproliferative effects of SRIF on tumor cell growth; therefore, they may mediate the clinical effects of Octreotide in humans. A recent comprehensive review of SRIF and its receptors is found in Patel, Y. C. "Somatostatin and its receptor family", *Front. Neuroendocrinol*, 1999, 20, 157–198. Pending U.S. patent application Ser. No. 09/607,546, filed Jun. 29, 2000, discloses SSTR3-selective synthetic analogs of SRIF. U.S. Pat. No. 5,750,499 (May 12, 1998) discloses SRIF analogs which are selective for SSTR1, and since that discovery, efforts have been made to discover analogs with even greater selectivity and/or greater binding strength.

Nonpeptide SRIF agonists have been identified using combinatorial chemistry which exhibit selectivity for each of SSTR1 to SSTR5, Rohrer, S. P. et al., *Science*, 282, 737–740, Oct. 23, 1998. However, improved peptide ligands continue to be sought because only peptide ligands can be satisfactorily derivatized to incorporate complexing agents for radionuclides. Additionally, peptides generally exhibit fewer undesirable side effects, such as toxicity or cross reactivity with unrelated receptors.

SUMMARY OF THE INVENTION

Certain modifications have now been discovered which are effective to create peptide analogs of SRIF that are more selective for SSTR1 in contrast to the other cloned human SRIF receptors and/or have greater binding strength than those disclosed in the '499 patent. The basic original modification substituted an optionally alkylated amino-methyl Phe into the 9-position of a SRIF analog that otherwise binds to SSTR1, and it has now been found that the selectivity and/or the binding strength of such analogs can be enhanced by modifying the N-terminus and/or the residue in the 11-position and also by $N^\alpha$methylating the alkylated 9-position residue. As a result, peptides have now been created that bind strongly and selectively to cloned SSTR1. Analogs of these peptides can be iodinated or otherwise radiolabeled while not only retaining their desirable biological properties, but certain iodinated Tyr-containing analogs show further increased binding strength. These novel peptides are useful in determining the tissue and cellular expression of the receptor SSTR1 and its biological role in the endocrine, exocrine and nervous system, as well as in regulating certain pharmacological functions without the accompanying side effects heretofore characteristic of administering SRIF. These long-acting SRIF analog peptides, when radiolabeled, can be used in scintigraphy in order to locate, i.e. localize, tumors expressing these receptors, either in vitro or in vivo; other labeling as well known in this art, e.g. fluorescent, can alternatively be used. With an appropriate chelated radioligand, these analogs can be turned into radiopharmaceuticals which are suitable for radionuclide therapy in treatment of such tumors; alternatively, they can be covalently joined to a cytotoxic moiety using an appropriate covalent conjugating agent, e.g. glutaraldehyde or one which binds via a disulfide linkage.

The SRIF analog peptides of the invention inhibit the binding of $^{125}$I-[Tyr$^{11}$]SRIF and $^{125}$I-[Leu$^8$, D-Trp$^{22}$,Tyr$^{25}$] SRIF-28 to the cloned human receptor SSTR1, but they do not bind with high affinity to SSTR2, SSTR3, SSTR4 or SSTR5. As such, these SSTR1 specific analogs may be used to treat conditions mediated by SSTR1, such as IH and other such SSTR1-mediated physiopathologies. Additional of these SRIF analogs which incorporate an iodinated tyrosine in position-2 of the native molecule also do not bind to SSTR2, 3, 4 or 5 but still bind potently and saturably to SSTR1. This is also true for analogs to which $^{99}$Tc, $^{111}$In or $^{90}$Y, for example, has been chelated by linkers, such as DOTA or DTPA, or to which other complexing or conjugating agents are linked to the N-terminus for the purpose of attaching moieties, e.g. cytotoxins, useful for diagnostic or therapeutic purposes. Conjugating agent is used herein to broadly refer to this class of well known chelating, complexing or otherwise covalently binding agents that serve to link desired moieties to peptides.

These SRIF analogs not only selectively bind to SSTR1, but they bind thereto with high affinity. By selectively binding is meant that they exhibit a $K_D$ or an $IC_{50}$ with SSTR1 which is at least about one-tenth or less of that with respect to at least 3 of the other five SRIF receptors. The greater the differential, the more preferred it is. It is believed the four residues located centrally within the ring structure, i.e. at positions 7–10 of the native molecule, are primarily responsible for receptor binding and biological activity; however, as herein shown both the N-terminus and the 11-position residue, along with these four residues, can have a significant effect thereupon. These SRIF analogs can also be readily labeled and effectively used in drug screening methods and in radionuclide and cytotoxic therapy. For example, these analogs are useful in localizing such receptor in the body and in diagnosing the locations of tumors, particularly prostate cancers, sarcomas and neuroendocrine tumors. As radionuclide therapeutic agents, they are considered to be particularly useful in destroying tumors expressing SSTR1 receptors.

DETAILED DESCRIPTION OF THE PREFERRED EMBODIMENTS

Unless defined otherwise, all technical and scientific terms used herein have the same meaning as is commonly understood by one of skill in the art to which this invention belongs. The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine.

SRIF analog peptides are provided having a selective affinity for the SRIF receptor SSTR1; and also have a high affinity for SSTR1, i.e. equal to a $K_D$ of about 35 nanomolar or less and preferably less than 10 nM. These peptides broadly encompass known analogs of SRIF, or obvious variations thereof, which have the 5-position residue deleted, have a D-isomer amino acid having an aromatic side chain in the position corresponding to the 8-position of the native peptide, and have an L-isomer aminomethylphenylalanine(Amp), preferably Amp(isopropyl), i.e. IAmp, in the adjacent position that corresponds to the 9-position of the native peptide. Improved binding strength has been found to result from the inclusion of one or more of the following modifications in the analogs described in the '499 patent; Tyr$^{11}$ or ITyr$^{11}$ is present, and/or the N-terminus is modified to create a urea group, with the 9-position residue being optionally $N^\alpha$methylated, e.g. $N^\alpha$MeIAmp. So long as the basic analog being modified exhibits SRIF properties by binding generally to SRIF receptors, insertion of $N^\alpha$MeIAmp or IAmp in the corresponding 9-position, (the insertion of a D-isomer amino acid in the 8-position if one should not already be present and the deletion of any residue in the 5-position should one be present), and the insertion of Tyr in the 11-position will create a molecule which is highly selective for the SSTR1 receptor and have good binding strength. Further improvements in binding strength will result from the optional modification at the N-terminus and the iodination of Tyr, i.e. ITyr, in the 11-position residue. The 1- and/or 2-position residues may be deleted to increase binding affinity to SSTR1 or may be replaced by Tyr or D-Tyr and/or a carbamoyl functionality may be included.

Since the characterization of SRIF, a large number of SRIF analogs have been synthesized having increased potency in some respect. Numerous U.S. patents have been issued disclosing such more potent SRIF analogs, and these analogs which include residues 3–4 and 6–14 can be rendered selective for the SSTR1 receptor by the incorporation of the modification of the present invention.

Examples of representative peptides exhibiting the desired specificity for SSTR1 are provided by the following amino acid sequence, which is based upon a numbering system consistent with the 14-residue sequence of native mammalian SRIF, but in which the residue at position 5 has been eliminated:

(cyclo 3-14)$Xaa_1$-$Xaa_2$-$Xaa_3$-Lys-Phe-$Xaa_7$-D-$Xaa_8$-$Xaa_9$-Thr-$Xaa_{11}$-Thr-$Xaa_{13}$-Cys wherein $Xaa_1$ is Ala, D-Ala, Cbm, Biu, (lower alkyl)Cbm, L-Hor, an acyl group having up to 20 carbon atoms, preferably 7 or less, e.g. 4-hydroxybenzoyl, lower alkyl or a conjugating agent, such as DOTA; $Xaa_2$ is Tyr, ITyr, D-Tyr, D-ITyr, Gly or des-Xaa; $Xaa_3$ is Cys or D-Cys; $Xaa_7$ is (A)Phe wherein A is H, Cl, F, Br, $NO_2$, Me or NH(Q) where Q is H, Cbm or L-Hor; and D-$Xaa_8$ is a D-isomer amino acid having an aromatic side chain; $Xaa_9$ is an aminomethyl Phe which is ($C_2$ to $C_5$)alkylated and which is optionally $N^\alpha$methylated; $Xaa_{11}$ is Phe, Tyr or ITyr; and $Xaa_{13}$ is Ser, $N^\alpha$MeSer or D-Ser; provided, however, that at least one of the following is present: (a) $Xaa_{11}$ is Tyr or ITyr; or (b) $Xaa_1$ is Cbm, Biu or (lower alkyl)Cbm, with $Xaa_9$ being optionally $N^\alpha$methylated. ITyr represents iodinated tyrosine, and when present at either position 2 or 11, its presence increases binding affinity whether radioiodinated or not. Of course, when radioiodinated, it acts as a tracer. As indicated, a conjugating/complexing agent can be linked to the α-amino group at the N-terminus of any of these peptide analogs, which agent is capable of joining thereto a radioactive nuclide or a cytotoxin. These conjugating/complexing agents may be any of those presently used which covalently bond to the α-amino group at the N-terminus of the analog. They may be designed to link, as by chelation, to a radioactive metal or to covalently bind to a cytotoxin, such as saporin, gelonin, ricin A chain, etc.

One preferred subgenus of SRIF analogs has the amino acid sequence:

(cyclo 3-14)$Xaa_1$-$Xaa_2$-$Xaa_3$-Lys-Phe-$Xaa_7$-D-$Xaa_8$-IAmp-Thr-$Xaa_{11}$-Thr-$Xaa_{13}$-Cys wherein $Xaa_1$ is H, Cbm, Biu or (lower alkyl)Cbm; $Xaa_2$ is Tyr, ITyr, D-Tyr or des-Xaa; D-$Xaa_8$ is either D-Trp or a substituted D-Ala wherein one hydrogen on the β-carbon is replaced by (a) a carbocyclic aryl-containing moiety selected from the group consisting of phenyl substituted with three or more straight chain lower alkyl groups, naphthyl, pyridyl, anthryl, fluorenyl, phenanthryl, biphenylyl and benzhydryl; or (b) a saturated carbocyclic moiety selected from the group consisting of cycloalkyl substituted with three or more straight chain lower alkyl groups, perhydronaphthyl, perhydrobiphenylyl, perhydro-2,2-diphenylmethyl, and adamantyl; and $Xaa_{11}$ is Tyr or ITyr. When not stated, the remaining variables should be understood to be as defined hereinbefore.

Another preferred subgenus of SRIF agonist peptides has the amino acid sequence:

(cyclo 3-14)$Xaa_1$-$Xaa_2$-Cys-Lys-Phe-Phe-D-$Xaa_8$-$N^\alpha$MeIAmp-Thr-Tyr-Thr-$Xaa_{13}$-Cys wherein $Xaa_1$ is H; $Xaa_2$ is des-Xaa; and D-$Xaa_8$ is either D-Trp or a D-Ala wherein one hydrogen on the β-carbon is replaced by (a) a carbocyclic aryl-containing radical selected from the group consisting of phenyl substituted with three or more straight chain lower alkyl groups, naphthyl, pyridyl, anthryl, fluorenyl, phenanthryl, biphenylyl and benzhydryl; or (b) a saturated carbocyclic radical selected from the group consisting of cycloalkyl substituted with three or more straight chain lower alkyl groups, perhydronaphthyl, perhydrobiphenylyl, perhydro-2,2-diphenylmethyl, and adamantyl; $Xaa_9$ is a ($C_3$ or $C_4$) alkylated aminomethyl Phe; and $Xaa_{11}$ is Tyr or ITyr.

An additional preferred subgenus of SRIF agonist peptides has the amino acid sequence:

(cyclo 3-14)$Xaa_1$-$Xaa_2$-Cys-Lys-Phe-Phe-D-$Xaa_8$-$N^\alpha$MeIAmp-Thr-Tyr-Thr-$Xaa_{13}$-Cys wherein $Xaa_1$ is Cbm, Biu, (lower alkyl)Cbm or H; $Xaa_2$ is des-Xaa; and D-$Xaa_1$ is (A)D-Trp where A is H or $NO_2$, or (B)D-Ala or (B)D,L-Ala where B is naphthyl, pyridyl, fluorenyl, adamantyl, anthryl, biphenyl, tri(lower alkyl)phenyl, pentamethylphenyl, phenanthryl, trialkylcyclohexyl, perhydronaphthyl or perhydrobiphenyl.

Still another preferred subgenus of SRIF agonist peptides has the amino acid sequence:

(cyclo 3-14)$Xaa_1$-$Xaa_2$-Cys-Lys-Phe-Phe-D-$Xaa_8$-$N^\alpha$MeIAmp-Thr-$Xaa_{11}$-Thr-$Xaa_{13}$-Cys wherein $Xaa_1$ is Cbm; $Xaa_2$ is Tyr, ITyr or 40 des-Xaa; D-$Xaa_8$ is D-Trp, D-2Nal, D-Me5-Phe, D-TMP, D-BIA, D-TBA, D-anthryl-Ala, D-fluorenyl-Ala or D-adamantyl-Ala; and $Xaa_{11}$ is Tyr or ITyr.

Another preferred subgenus of SRIF analogs has the amino acid sequence:

(cyclo 3-14)$Xaa_1$-$Xaa_2$-$Xaa_3$-Lys-Phe-$Xaa_7$-D-$Xaa_8$-$N^\alpha$MeIAmp-Thr-$Xaa_{11}$-Thr-$Xaa_{13}$-Cys wherein $Xaa_1$ is Cbm, a chelating agent, or H; $Xaa_2$ is des-Xaa; and D-Xaa8 is D-Trp or D-Nal.

An additional preferred subgenus of SRIF analogs has the amino acid sequence:

(cyclo 3-14)D-Cys-Lys-Phe-$Xaa_7$-D-$Xaa_8$-IAmp-Thr-$Xaa_{11}$-Thr-$Xaa_{13}$-Cys wherein $Xaa_7$ is Phe or $4NO_2$Phe; D-$Xaa_8$ is D-Trp; $Xaa_{11}$ is Tyr or ITyr and IAmp is optionally $N^\alpha$methylated.

Still another preferred subgenus of SRIF analogs has the amino acid sequence:

(cyclo 3-14)$Xaa_1$-$Xaa_2$-$Xaa_3$-Lys-Phe-$Xaa_7$-D-$Xaa_8$-$N^\alpha$MeIAmp-Thr-$Xaa_{11}$-Thr-$Xaa_{13}$-Cys wherein $Xaa_1$ is Cbm or H; $Xaa_2$ is des-Xaa; D-$Xaa_8$ is D-Trp or D-2Nal; $Xaa_{11}$ is Tyr or ITyr; and $Xaa_{13}$ is $N^\alpha$MeSer.

By D-Nal is meant the D-isomer of alanine which is substituted by naphthyl on the β-carbon atom. D-2Nal, wherein the attachment to naphthalene is at the 2-position on the ring structure, is preferable, and D-1Nal is less desirable. Cbm stands for carbamoyl and is preferred; however, lower alkyl carbamoyl, e.g. methyl, isopropyl, butyl, etc., are considered to be equivalents. Biu represents biuret which is carbamoyl urea $NH(CONH_2)_2$. Pal represents alanine which is substituted by pyridyl on the β-carbon atom; preferably the linkage is to the 3-position on the pyridine ring. When substituted D-Trp is employed, single substitutions for hydrogen are preferably made in either the 5- or 6-position, which are selected from chloro, fluoro, bromo and nitro, with chloro, fluoro and nitro being preferred. Alternatively, the indole nitrogen may be acylated with formyl ($N^{in}$For- or 1For-). By Amp is meant (aminomethyl)phenylalanine; unless otherwise specified, the methyl group with its amino substitution should be understood to be in the 4- or para-position on the phenyl ring. By IAmp is meant (N-isopropylaminomethyl)phenylalanine, where the 4-aminomethyl group is alkylated with an isopropyl group; in EAmp, the alkylation is with an ethyl group. By D-Me5Phe is meant 3-(2,3,4,5,6-pentamethylphenyl)-D-Ala. By D-TMP is meant 3-(2,4,6-trimethylphenyl)-D-Ala. By D-BIA is meant 3-(benzimidazol-2-yl)-D-Ala. By D-TBA is meant 3-(4,5,6,7-tetrahydrobenzimidazol-2-yl)-D-Ala.

As used herein, the term "lower alkyl" refers to a straight or branched chain, saturated hydrocarbon group having from 1 to 6 carbon atoms such as, for example, methyl, ethyl, n-propyl, isopropyl, n-butyl, isobutyl, sec-butyl, tert-butyl, isopentyl, n-pentyl and n-hexyl; the term "cycloalkyl group" refers to a cyclic saturated hydrocarbon group having from 4 to 6 carbon atoms, e.g. cyclobutyl, cyclopentyl and cyclohexyl. As used herein, "naphthyl" is inclusive of 1- and 2-naphthyl; "anthryl" is inclusive of 1-, 2- and 9-anthryl; "fluorenyl" is inclusive of 2-,3-,4- and 9-fluorenyl; "phenanthryl" is inclusive of 2-,3- and 9-phenanthryl; and "adamantyl" is inclusive of 1- and 2-adamantyl. By Me is meant methyl. By Bzl is meant benzyl, and by Bz is meant benzoyl. By Ac is meant acetyl, and by Np is meant naphthoyl. As used herein, naphthoyl is inclusive of 1- and 2-naphthoyl, with 2-naphthoyl being preferred. By Hor is meant the L-isomer of hydroorotic acid. By SRIF is meant the 14-residue cyclic peptide, somatostatin.

The C-terminus is usually free acid, although an equivalent, e.g. OMe or $NH_2$, might be used. The N-terminus may be modified in various ways without significantly adversely effecting the binding affinity, all of which modifications in these cyclic peptides are considered to be included as a part of the peptides of the overall invention. For example, a variety of additions may be made to the N-terminal amino acid in the form of conjugating agents which can be then used to link a desired moiety to the peptide. For example, chelating agents, such as DTPA, DOTA, HYNIC and $P_2S_2$-COOH may be attached; alternatively, a cytotoxin may be covalently linked thereto via a suitable linker well known in this art if desired. When Tyr or D-Tyr appears at the N-terminus, it may be radioiodinated or otherwise labeled, and iodination of $Tyr^{11}$ has been shown to increase binding affinity. Acyl groups having not more than about 20 carbon atoms, but preferably having not more than 7, e.g. 4-hydroxybenzyl, may also be present at the N-terminus, as bulky moieties appear to be accommodated without loss of affinity and selectivity. Alternatively, the N-terminus may be alkylated with lower alkyl. Moreover, the addition of Cbm, lower alkyl Cbm or Biu is considered to increase binding strength.

Although SSTR1 was the first somatostatin receptor cloned, identification of its biological and pharmacological properties has lagged somewhat behind the other SRIF receptors because of the lack of ligands which are significantly selective for SSTR1. The peptides of the invention are believed to be improvements over those disclosed in the '499 patent and they should be very helpful in determining the many functional roles of this receptor and in selectively binding only this SRIF receptor and not the others. They should be valuable in treating IH, and they will be particularly valuable in SRIF receptor-targeted scintigraphy and radionuclide therapy. For a number of reasons it is considered advantageous to have peptide, rather than nonpeptide, ligands of this character.

Selectivity for binding of the analog peptides of the invention to SSTR1 is demonstrated by testing their interaction with the five different cloned human SRIF receptors as described in great detail hereinafter. Generally, recombinant cells expressing the receptor are washed and homogenized to prepare a crude protein homogenate that is frozen, embedded and then cut in 10–20 μm thin sections, as known in this art. Candidate substances, such as potential SRIF agonists and antagonists, are incubated with the tissue sections, and the interaction between the candidate substance and the receptor polypeptide is monitored. The peptides of the invention bind substantially only to SSTR1, and their binding exhibits high affinity.

Receptor binding assays are performed on cloned SRIF receptors as generally set forth in Reubi, J. C. et al., *J. Clin. Endocrinol. Metab.*, 63, 433–438 (1986) and in Reubi, J. C. et al., *Eur. J. Nucl. Med.* 2000, 27, 273–282. Using such assays, one can generate $K_D$ values which are indicative of the concentration of a ligand necessary to occupy one-half (50%) of the binding sites on a selected amount of a receptor or the like, or alternatively, competitive assays can generate $IC_{50}$ values which are indicative of the concentration of a competitive ligand necessary to displace a saturation concentration of a target ligand being measured from 50% of binding sites. The peptide des-$AA^{1,2,5}$-[D-Trp8, $N^\alpha MeIAmp^9$, $Tyr^{11}$]SRIF inhibits the binding to SSTR1 of an iodinated SRIF-28 ligand that has strong affinity for all five receptors. Testing shows that it binds to the cloned human SSTR1 with an $IC_{50}$ of about 6.1 nM, while this SRIF analog peptide does not bind strongly to human SSTR3 or SSTR4 and does not bind to SSTR2 or SSTR5 at a concentration below 10,000 nM.

When such a SRIF analog is modified to have its tyrosine residue in position-11 radioiodinated, the $^{125}I$-$Tyr^{11}$ analog likewise does not bind any more strongly to SSTR2, 3, 4 or 5, but surprisingly it now binds even more strongly to SSTR1. The similar analog, des-$AA^{1,2,5}$-[D-$Nal^8$, $N^\alpha MeIAmp^9$, $Tyr^{11}$]-SRIF inhibits binding of the same iodinated SRIF-28 ligand to SSTR1 and binds itself with an $IC_{50}$ of about 21 nM, while not binding to receptors SSTR2, SSTR4 or SSTR5 at concentrations below 10,000 nM or to SSTR3 at a concentration below 1,000 nM. These SRIF analogs that selectively show high affinity to SSTR1 are considered to be particularly useful in the treatment of IH and other SSTR1-mediated physiopathologies and in combating tumors by carrying radionuclides or cytotoxins to the sites of these receptors but not to other SRIF receptors.

As hereinbefore indicated, SSTR1 mRNA has been detected in a variety of tumors. However, it is presently not known whether SSTR1 plays a major role in tumor growth regulation and, if it does, whether it mediates stimulation or inhibition. Therefore, it is difficult to foretell whether a selective SSTR1 antagonist would have a beneficial role for long-term treatment of tumors. However, the use of SRIF analogs selective for SSTR1 that bind strongly thereto, and that are long-acting can be effectively used to kill such tumors via radionuclide or cytotoxic therapy. To date the use of Octreotide in the treatment of such tumors has not been considered to be satisfactorily effective particularly because of its selectivity to SSTR2, 3 and 5.

Although the binding of the SRIF analogs of the invention to SSTR1 is potently inhibited by native SRIF and by SRIF-28, it is not inhibited by many other synthetic SRIF analogs. Moreover, the lack of strong binding of the peptides of the invention to SSTR4 is of particular interest because SSTR1 and SSTR4 have approximately 68% amino acid sequence identity, which constitutes higher sequence similarity than for any other two SRIF receptors. Furthermore, SSTR1 and SSTR4 both exhibit very low affinity for a large number of other synthetic analogs of SRIF which bind potently to SSTR2, SSTR3 and SSTR5. The high amino acid sequence similarity and similar ligand binding characteristics would usually have predicted that these two SRIF receptors would share some common structural similarities in ligand-binding domains; however, the fact that the peptides of the invention selectively bind only to SSTR1 indicates that there may be considerable differences in ligand-binding properties between these two otherwise structurally similar receptors.

SSTR1 has been reported to couple to a tyrosine phosphatase, and stimulation of this enzyme is believed to mediate anti-proliferative effects of SRIF via activation of this receptor. SSTR1 mRNA has been detected in a number of tumors. The ability of SSTR1 to mediate anti-proliferative effects of SRIF renders SSTR1-selective SRIF agonists effective as therapeutic treatment agents for treating those cancers, such as prostrate cancers and sarcomas wherein the malignant tissues express this receptor.

A particularly important advantage of SSTR1-selective agonists as anti-cancer agents may be their continued effectiveness after prolonged use. Continuous use of SMS-201-995 in the treatment of tumors is considered to be hindered by rapid desensitization of SSTR2, SSTR3 and SSTR5, the receptors this peptide can interact with; in fact, all 3 of these receptors have been reported to rapidly desensitize. In contrast, studies suggest that SSTR1 may be more resistant to agonist-induced regulation than the other receptors. As a result, the SSTR1-selective peptide agonists of the invention are considered to have prolonged anti-proliferative actions and should therefore exhibit improved effectiveness in treating SSTR1-mediated cancers, compared to the commercially available SRIF analogs presently used as anti-cancer agents that have low affinity for SSTR1.

Furthermore, an analog of SMS-201-995 has recently been employed to detect human tumors having high expression of SRIF receptors through the use of positron-emission tomography. This SRIF analog does not distinguish among SSTR2, SSTR3 or SSTR5, and it is unlikely to be able to detect SSTR1 expression. Labelled SRIF analogs of the present invention can be employed for similar purposes and are considered to be specifically useful in identifying tumors expressing SSTR1, which tumors would then be therapeutic targets for treatment with SSTR1-selective ligands.

While SSTR1 has the typical structure of other G protein-linked receptors, controversy exists over whether this receptor truly associates with G proteins and effectively couples to adenylyl cyclase. Some investigators have reported that SRIF binding to this receptor is not affected by GTP analogs or pertussis toxin and does not effectively couple to adenylyl cyclase, whereas others have reported opposite findings. Furthermore, some investigators have failed to show GTP analog regulation of agonist binding to the receptor but have found that receptor mediates the inhibition of cAMP formation by SRIF; however, this may have been a function of the particular cell systems that were used.

The SRIF analogs of the present invention are considered to be useful in combating cancers which express SSTR1 and in combating IH and other SSTR1-mediated physiopathologies. They are also considered to be most useful in scintigraphy to determine the distribution of cells and tissues expressing this receptor in the brain and in the endocrine and exocrine systems, and also in identifying selective functions of this receptor in the body.

Labeled SRIF analogs of the invention are also considered to be useful in drug-screening assays to screen for new effective peptide and nonpeptide agents which will bind with high affinity to SSTR1 and which may be either highly effective agonists or antagonists for treating GI track motility. Once a known ligand for the receptor SSTR1 is in hand, one can obtain a baseline activity for the recombinantly produced receptor. Then, to test for inhibitors or modifiers, i.e. antagonists of the receptor function, one can incorporate into a test mixture a candidate substance to test its effect on the receptor. By comparing reactions which are carried out in the presence or absence of the candidate substance, one can then obtain information regarding the effect of the candidate substance on the normal function of the receptor. The cyclic SRIF analogs described in the following examples are agonists which can be employed to selectively stimulate the inhibitory activity of somatostatin at SSTR1.

The peptides of the present invention can be synthesized by classical solution synthesis, but they are preferably synthesized by solid-phase technique, as described in U.S. Pat. No. 5,750,499 issued May 12, 1998, the disclosure of which is incorporated herein by reference.

The SRIF analogs of the invention are generally effective at levels of less than 100 micrograms per kilogram of body weight. For prolonged action, it may be desirable to use dosage levels of about 0.1 to about 2.5 milligrams per kilogram of body weight. These analogs are soluble in water and thus can be prepared as relatively concentrated solutions for administration.

The following Examples illustrate the syntheses of a number of SRIF analog peptides embodying various features of the invention, together with the syntheses of protected amino acids for use in such peptide syntheses. All of these peptides include at least one D-isomer amino acid residue, and although the preferred SRIF analogs do not include all 14 amino acid residues of the native SRIF, to permit ready comparison with the native SRIF sequence, the peptide analogs are described by making reference to the comparable positions in the native SRIF sequence having positions 1 through 14, as is commonly done when naming analogs of a native compound. In each peptide, "cyclo" indicates that the two cysteine residues are joined by a cyclizing disulfide bond.

EXAMPLE 1

Synthesis of $N^{\alpha}$MeBoc-4aminomethylPhe(ipr)

The synthesis of L-$N^{\alpha}$-MeBoc-$N^{4}$-Cbz-(4-isopropylaminomethyl)phenylalanine, which is referred to by the shorthand nomenclature as Boc-$N^{\alpha}$MeIAmp(Z), is carried out as follows:

L-$N^{\alpha}$-Boc-(4-aminomethyl)phenylalanine (Boc-Amp) (15.3 g, 52 mmol) is dissolved in acetone (200 mL), and molecular sieves (6.0 g, 4 Å) are added to the solution in a 500 mL Parr hydrogenation vessel. The mixture is purged with $N_2$ for 10 minutes; then Pd/C 10% (600 mg) is added. A reductive alkylation reaction occurs and is monitored by HPLC; it is carried out for about 26 hours. After filtration to remove the catalyst and molecular sieves and evaporation of the solvent, the desired intermediate L-$N^{\alpha}$-Boc-(4-isopropylaminomethyl)phenylalanine is obtained as a viscous liquid.

The product is then Cbz-protected using benzyl chloroformate (Z-Cl, 8.6 mL, 60 mmol) in a mixture of THF/$H_2O$ (1:1,200 mL) at pH=9.5. A good yield of L-$N^{\alpha}$-Boc-$N^{4}$-Cbz-(4-isopropylaminomethyl)phenylalanine is obtained as a foam: 17.5 g (37 mmol, 71.4%); m.p. 39–42° C.; $[\alpha]_D$=+5.2° (c=1, MeOH, t=20° C.).

The product is the $N^{\alpha}$methylated by dissolution in a suitable solvent, e.g., THF, and treated with methyl iodide and sodium hydride (NaH). For example, 0.152 mole of the product is dissolved in 100 milliliters of tetrahydrofuran (THF) and added dropwise to 13.58 grams of NaH(0.452 mole) (3 eq) which was dissolved in 500 milliliters of THF at 0° C. Thereafter, 42.6 grams of methyl iodide (2 eq), dissolved in THF, are added dropwise over 30 minutes, and stirring in a beaker is continued for about 36 hours at room temperature. The reaction is stopped by placing the beaker in an ice bath and by the slow addition of 20 milliliters of glacial acetic acid and 20 milliliters of distilled water. The THF is removed by rotary evaporation, and the remaining oil is diluted with 300 milliliters of water. After adjusting to a pH of about 8 with sodium carbonate, the mixture is extracted twice, using 200 milliliters of ethyl ether each time. Following extraction, the remainder is acidified to a pH of about 2 with sulfuric acid, and it is then extracted twice with 300 milliliters of ethylacetate. After drying over anhydrous magnesium sulfate, solvent removal is effected by evaporation, giving about 40 grams of an oil which crystallizes to crystals of Boc-N$^\alpha$MeIAmp(Z)

EXAMPLE 2

The somatostatin agonist des-AA$^{1,2,5}$[D-Trp$^8$, N$^\alpha$MeIAmp$^9$, Tyr$^{11}$]-SRIF having the structure:

(cyclo)H-Cys-Lys-Phe-Phe-D-Trp-N$^\alpha$MeIAmp-Thr-Tyr-Thr-Ser-Cys-OH is synthesized by the solid phase methodology in a stepwise manner on a chloromethylated resin generally as described in Example 2 of the '499 patent. For the 9-position residue, the monomer synthesized in Example 1, i.e. N$^\alpha$(Boc)Me-4-isopropylaminomethyl Phe(z) is coupled into the chain. This synthesis creates the intermediate: Boc-Cys (Mob)-Lys(2-ClZ)-Phe-Phe-D-Trp-N$^\alpha$MeIAmp(Z)-Thr(Bzl)-Tyr(2BrZ)-Thr(Bzl)-Ser(Bzl)-Cys (Mob)-O-CH$_2$-resin support.

Cleavage of the peptide from the resin and deprotection of the side chain protecting groups are performed in hydrofluoric acid(HF) (25 ml) in the presence of 10% of anisole and 5% of methylsulfide for 1.5 hours at 0° C. after 20 minutes at ambient temperature. After elimination of hydrofluoric acid under high vacuum, the resin-peptide is washed with anhydrous diethyl ether.

The resin is immediately extracted with 75% acetic acid (200 ml). The extract is filtered into a 500 milliliter round-bottom flask and is then oxidized to create the disulfide cyclic linkage by stirring vigorously while rapidly adding a 10 weight percent solution of iodine in methanol until the resultant solution remains orange-colored. It is then stirred for 40 additional minutes and quenched with 10% ascorbic acid in water until the yellow color is gone. Concentration under vacuum is carried out to reduce the volume to about 50 milliliters, followed by dilution to about 300 milliliters with water. The solution is then applied to a 4 centimeter by 7 centimeter pad of C$_{18}$ silica in a coarse-fritted funnel that was previously equilibrated with 5% CH$_3$CN in 0.1% trifluoroacetic acid (TFA) in water. Following vacuum filtration, the eluate is diluted to 500 milliliters and reapplied to the pad. The eluate is collected and diluted to about 800 ml, and filtration is repeated. Thereafter, the pad is washed with about 300 milliliters of 5% acetonitrile in 0.1% TFA, and the peptide is eluted using about 250 milliliters of 60% CH$_3$CN in water. The resultant solution is diluted to about 500 milliliters with distilled water, frozen and lyophilized.

The lyophilized crude peptides were purified by preparative RP-HPLC using a linear gradient 1% B per 3 min. increase from the baseline % B (Eluent A=0.25 N TEAP pH 2.25, eluent B=60% CH$_3$CN, 40% A) at a flow rate of 100 mL/min. Peaks are located which are then individually purified using buffer systems as disclosed in Hoeger et al., *Biochromatography,* 2, 134–142 (1987). Purification in TEAP pH 2.25 was followed by a rechromatography in a 0.1% TFA solution and acetonitrile on the same cartridge (gradient of 1% acetonitrile/min.). The separations were monitored by analytical RP-HPLC at 215 nm. The fractions containing the pure product were pooled and lyophilized to obtain a fluffy white powder. The desired cyclic peptide (cyclo)H-Cys-Lys-Phe-Phe-D-Trp-N$^\alpha$MeIAmp-Thr-Tyr-Thr-Ser-Cys-OH is obtained which appears to be greater than 98% pure on capillary zone electrophoresis.

MS analysis shows a mass of 1515.6 Da which compares favorably to the calculated mass of 1514.7 Da. The peptide is hereinafter referred to as Peptide No. 2.

EXAMPLES 2A AND 2B

The synthesis described in Example 2 is repeated with one change; instead of using N$^\alpha$(Boc)Me-4-isopropylaminomethyl Phe(Z) for the 9-position residue, Boc-4-isopropylamino Phe(Z), which is also referred to as Boc-IAmp(Z), is used. Cleavage, deprotection, cyclization and purification are carried out as in Example 2. A purified cyclic peptide having the formula:

(cyclo)H-Cys-Lys-Phe-Phe-D-Trp-IAmp-Thr-Tyr-Thr-Ser-Cys-OH is obtained which appears to be greater than 98% pure on capillary zone electrophoresis. It is referred to as Peptide 2A. MS analysis shows a mass of 1501.5 Da which compares favorably with the calculated mass of 1500.66 Da.

A portion of the product Peptide 2A above is taken and subjected to iodination as well known in this art to iodinate the Tyr$^{11}$. The iodinated compound is thereafter referred to as Peptide 2B. Radioactive iodination is instead used when desired to create a tracer. MS analysis shows a mass of 1627.5 Da which compares favorably to the calculated mass of 1626.55 Da.

EXAMPLE 3

The initial synthesis described in Example 2 is repeated with one change; N$^\alpha$Boc-N$^4$-Fmoc-(4-aminomethyl)phenylalanine, i.e. Boc-Amp(Fmoc), is used to provide the 9-position residue. The Boc group is removed, and the α-amino group of the Amp residue is N-alkylated on the resin as described in Kaljuste and Unden, *Int. J. Peptide Protein Res.,* 42, 118–124 (1993). Further elongation of the chain then proceeds as in Example 2, until the final coupling with Boc-Cys(Mob) is effected.

With the N$^\alpha$Boc group still in place at the N-terminus, the side chain of Amp is alkylated. The Fmoc protecting group is selectively removed by treatment with 20 percent piperidine in NMP or DMF(10 ml.) for about 15 minutes; the intermediate is preferably washed with NMP and then treated with more piperidine/NMP for another 15 minutes. After preferably washing the peptidoresin with NMP, the newly freed aminomethyl groups are treated with Meophenyl)$_2$-CHCl, which is referred to as Dod-Cl, in NMP plus diisopropyl ethylamine (DIEA) for 1–2 hours. After washing, the peptidoresin (about 1–2 g) is treated for 20 minutes with 15 mls of a solution of 40% acetaldehyde in 1% acetic acid in NMP, plus 0.35 gm. of cyanoborohydride and repeated once. This reaction, details of which reaction can be found in Kaljuste, supra, adds a single ethyl group to the aminomethylPhe side chain. The usual washing is carried out, and then the Dod-Cl protecting group and the Boc group at the N-terminus are removed by treatment with 60% TFA in DCM for 20 minutes. Cleavage, deprotection, cyclization and purification are then carried out as in Example 2. The purified cyclic peptide has the formula:

(cyclo)H-Cys-Lys-Phe-Phe-D-Trp-N$^\alpha$MeEAmp-Thr-Tyr-Thr-Ser-Cys-OH and is referred to as Peptide No. 3.

EXAMPLE 4

The synthesis described in Example 2 is used to produce about 4 grams of product with two changes. N$^\alpha$Boc-D-Cys (Mob) is used to provide the 3-position residue, and an alternative cyclization step is used. Following removal of the Boc group at the N-terminus, cleavage and deprotection are carried out as in Example 2. Cyclization is then effected by dissolving four grams of the deprotected linear somatostatin analog in 2.500 ml of five percent acetic acid having a pH of 3. Two and a half grams of potassium ferricyanide is dissolved in one and a half liter of water containing five grams of ammonium acetate and having a pH of 6.9. The peptide solution is added dropwise to the ferricyanide solution at a rate of 140 ml per hour while the reaction mixture is constantly stirred under nitrogen.

A pH stat is used to monitor the pH of the reaction mixture, and the pH is maintained in the range of 6.8–7 throughout the reaction by the addition of a 10 percent ammonium hydroxide solution, as required. After addition of the last increment of the peptide solution, the reaction is continued for 2 hours under conditions of constant stirring.

The pH is then reduced to 5 with acetic acid, and the yellowish, greenish slightly turbid solution is filtered over celite. The filtered solution is then applied onto and filtered through a weakly basic anion exchange resin (Bio Rad AG3 ×4A column, 100–200 mesh, chloride form –300 ml) under mild suction. All of the ferro and ferricyanide anion is removed in this step. The clear solution (4–5 liters, including the different washes used in the celite filtration and the anion exchange transfer) is applied onto a weakly acidic carboxylic cation exchange resin (Bio Rex 70 column, 200 ml—acidic form) which runs overnight. The following morning 90 percent of the peptide has been retained on the cation exchange column. The retained peptide is washed with 200 ml of 5 percent acetic acid. The peptide is then eluted from the cation exchange column by washing the column with 500 ml of 50 percent acetic acid. The peptide containing fractions (about 200 ml) are concentrated on a rotary evaporator to a volume of 30 ml. The peptide is then lyophylized after dilution with water. Purification is then effected as in Example 2. The purified cyclic peptide has the formula:

(cyclo)H-D-Cys-Lys-Phe-Phe-D-Trp-N$^\alpha$MeIAmp-Thr-Tyr-Thr-Ser-Cys-OH and is referred to as Peptide No. 4.

EXAMPLE 5

The synthesis described in Example 2 is repeated with one change. Boc-4NO$_2$-Phe is used instead of N$^\alpha$Boc-Phe to provide the 7-position residue. Further elongation of deprotection, cyclization and purification are carried out as in Example 2. The purified, cyclic peptide has the formula:

(cyclo)H-Cys-Lys-Phe-4No$_2$Phe-D-Trp-N$^\alpha$MeIAmp-Thr-Tyr-Thr-Ser-Cys-OH and is referred to as Peptide No. 5.

EXAMPLE 5A

The synthesis described in Example 5 is repeated with two changes. Boc-IAmp(z) is used as the 9-position residue, and N$^\alpha$Boc-D-2Nal is used as the 8-position residue. Cleavage, deprotection, cyclization and purification are carried out as in Example 2, and the purified cyclic peptide has the formula:

(cyclo)H-Cys-Lys-Phe-4NO$_2$Phe-D-2Nal-IAmp-Thr-Tyr-Thr-Ser-Cys-OH MS analysis shows a mass of 1541.6 Da which compares favorably to the calculated mass of 1540.65 Da. The peptide is hereinafter referred to as Peptide No. 5A.

EXAMPLE 6

The synthesis described in Example 2 is repeated with one change. N$^\alpha$Boc-4Cl-phenylalanine, i.e. Boc-4ClPhe, is used to provide the 7-position residue. Further elongation of the chain then proceeds as in Example 2, and cleavage, deprotection, cyclization, and purification are carried out as in Example 2. The purified, cyclic peptide has the formula:

(cyclo)H-Cys-Lys-Phe-4ClPhe-D-Trp-N$^\alpha$MeIAmp-Thr-Tyr-Thr-Cys-OH and is referred to as Peptide No. 6.

EXAMPLE 7

The synthesis described in Example 5 is repeated with one change. N$^\alpha$Boc-D-Cys(Mob) is used to provide the 3-position residue. Following removal of the Boc group at the N-terminus, cleavage, deprotection, cyclization, and purification are carried out as in Example 2. The purified, cyclic peptide has the formula:

(cyclo)H-D-Cys-Lys-Phe-4NO$_2$Phe-D-Trp-N$^\alpha$MeIAmp-Thr-Tyr-Thr-Ser-Cys-OH and is referred to as Peptide No. 7.

EXAMPLE 8

The synthesis described in Example 4 is repeated with one change. N$^\alpha$Boc-Phe is used to provide the 11-position residue. Following removal of the Boc group at the N-terminus, cleavage, deprotection, cyclization, and purification are carried out as in Example 2. The purified cyclic peptide has the formula:

(cyclo)H-D-Cys-Lys-Phe-Phe-D-Trp-N$^\alpha$MeIAmp-Thr-Phe-Thr-Ser-Cys-OH and is referred to as Peptide No. 8.

EXAMPLE 9

The synthesis described in Example 2 is repeated with one change. Instead of coupling Boc-D-Trp as what is referred to as the 8-position residue, N$^\alpha$Boc-D-2Nal is used. Further elongation of the chain then proceeds as in Example 2.

Cleavage, deprotection, cyclization and purification are carried out as in Example 2. Amino acid analysis shows the expected ratio for the different amino acids. The purified cyclic peptide has the formula:

(cyclo)H-Cys-Lys-Phe-Phe-D-2Nal-N$^\alpha$MeIAmp-Thr-Tyr-Thr-Ser-Cys-OH and is referred to as Peptide No. 9A. MS analysis shows a mass of 1526.6 Da, which compares favorably to the calculated value 1525.7.

The synthesis is repeated, substituting N$^\alpha$Boc-D-1Nal for N$^\alpha$Boc-D-2Nal to obtain the following purified cyclic peptide, which is referred to as Peptide No. 9B:

(cyclo)H-Cys-Lys-Phe-Phe-D-1Nal-N$^\alpha$MeIAmp-Thr-Tyr-Thr-Ser-Cys-OH

EXAMPLE 10

The synthesis described in Example 2 is repeated with one change. Instead of coupling Boc-Ser(Bzl) as what is referred to as the 13-position residue, $N^\alpha$Boc-D-Ser(Bzl) is used. Elongation of the chain is then carried out as in Example 2.

Cleavage, deprotection, cyclization and purification are carried out as in Example 2. A purified cyclic peptide having the formula:

(cyclo)H-Cys-Lys-Phe-Phe-D-Trp-$N^\alpha$MeIAmp-Thr-Tyr-Thr-D-Ser-Cys-OH and is referred to as Peptide No. 10.

EXAMPLE 11

The synthesis described in Example 2 is repeated with one change. Instead of coupling Boc-D-Trp as what is referred to as the 8-position residue, $N^\alpha$Boc-D-3-Pal is used. Elongation of the chain is then carried out as in Example 2.

Cleavage, deprotection, cyclization and purification are carried out as in Example 2. The purified cyclic peptide has the formula:

(cyclo)H-Cys-Lys-Phe-Phe-D-3Pal-$N^\alpha$MeIAmp-Thr-Tyr-Thr-Ser-Cys-OH and is referred to as Peptide No. 11.

EXAMPLE 12

The synthesis described in Example 2 is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction is carried out with about 1 gm of the peptidoresin and 100 mg of sodium cyanate (NaOCN) and acetic acid (3 ml) for 30 minutes at 22° C. in NMP (4 ml). This reaction results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo)CbmCys-Lys-Phe-Phe-D-Trp-$N^\alpha$MeIAmp-Thr-Tyr-Thr-Ser-Cys-OH and is referred to as Peptide No. 12. MS analysis shows a mass of 1558.7 Da, which compares favorably to the calculated value of 1557.7.

EXAMPLES 12A AND 12B

The synthesis set forth in Example 12 is repeated substituting Boc-IAmp(Z) for the 9-position residue. Cleavage, deprotection, cyclization and purification of the peptide are carried out as in Example 2. The purified cyclic peptide has the formula:

(cyclo)CbmCys-Lys-Phe-Phe-D-Trp-IAmp-Thr-Tyr-Thr-Ser-Cys-OH. The peptide is hereinafter referred to as Peptide No. 12A. MS analysis shows a mass of 1544.6 Da, which compares favorably with the calculated value of 1543.66 Da. A portion of the peptide synthesized is then subjected to iodination in the normal manner so as to iodinate the Tyr[11]. MS analysis shows a mass of 1670.6 Da which compares favorably to the calculated value of 1669.57 Da for a nonradioiodinated peptide. To provide a tracer, $^{125}$I may be used. This peptide is referred to hereinafter as Peptide No. 12B.

EXAMPLE 12C

The synthesis set forth in Example 12A above is repeated with one change. $N^\alpha$Boc-D-Cys(Mob) is used to provide the 3-position residue. Cleavage, deprotection, cyclization and purification are carried out as in Example 2, and the purified cyclic peptide has the formula:

(cyclo)CbmD-Cys-Lys-Phe-Phe-D-Trp-IAmp-Thr-Tyr-Thr-Ser-Cys-OH. The peptide is hereinafter referred to as Peptide No. 12C. MS analysis shows a mass of 1544.6 Da, which compares favorably to the calculated value of 1543.66 Da.

EXAMPLE 12D

The synthesis set forth in Example 12 is repeated with one change. $N^\alpha$Boc-ITyr(2BrZ) is used to provide the 11-position residue. Cleavage, deprotection, cyclization and purification are carried out as in Example 2, and the purified cyclic peptide has the formula:

(cyclo)CbmCys-Lys-Phe-Phe-D-Trp-$N^\alpha$MeIAmp-Thr-ITyr-Thr-Ser-Cys-OH. The peptide is hereinafter referred to as Peptide No. 12D. MS analysis shows a mass of 1684.6 Da, which compares favorably to the calculated value of 1684.59 Da. If desired for use as a tracer, radioactive ITyr is used.

Peptides 2–12D bind strongly and selectively to human SSTR1.

EXAMPLE 13

The synthesis described in Example 2 is repeated but this time $N^\alpha$Boc-Phe is used instead of $N^\alpha$Boc-Tyr(2BrZ) for the 11-position to produce the 11-residue peptide. Cleavage, deprotection, cyclization, and purification are carried out as in Example 2. The purified cyclic peptide has the formula:

(cyclo)H-Cys-Lys-Phe-Phe-D-Trp-$N^\alpha$MeIAmp-Thr-Phe-Thr-Ser-Cys-OH and is referred to as Peptide No. 13. MS analysis shows a mass of 1499.8 Da, which compares favorably to the calculated value of 1498.7.

EXAMPLE 14

The synthesis described in Example 13 is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 12 is carried out and results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo)CbmCys-Lys-Phe-Phe-D-Trp-$N^\alpha$MeIAmp-Thr-Phe-Thr-Ser-Cys-OH and is referred to as Peptide No. 14.

EXAMPLES 14A AND 14B

The synthesis described in Example 14 is repeated with two changes. Boc-IAmp(Z) is used to provide the 9-position residue, and subsequent to the coupling of the Cys residue in the 3-position, the chain is elongated by one residue by coupling $N^\alpha$Boc-Tyr(2BrZ) at the N-terminus. Following removal of the Boc group after the coupling of the Tyr residue, a reaction is carried out to add a carbamoyl moiety and thus create an urea group at the N-terminus as in Example 14. Cleavage, deprotection, cyclization and purification are carried out as in Example 2. The purified cyclic peptide has the formula:

(cyclo)CbmTyr-Cys-Lys-Phe-Phe-D-Trp-IAmp-Thr-Phe-Thr-Ser-Cys-OH. MS analysis shows a mass of about 1691.8 Da which compares favorably with the calculated mass of 1690.73 Da. The peptide is referred to hereinafter as Peptide No. 14A.

A portion of the peptide is then subjected to standard iodination so as to iodinate the tyrosine in the 2-position. MS analysis shows a mass of about 1817.8 Da which compares favorably with the calculated mass of 1816.64 Da. The iodinated peptide is hereinafter referred to as Peptide No. 14B. Of course $^{125}$I may be used to provide a tracer.

EXAMPLE 14C

The synthesis as described with respect to Example 14A is repeated with one change. Boc-D-Cys(Mob) is used to provide the 3-position residue. Following the reaction to create the carbamoyl moiety at the N-terminus, cleavage, deprotection, cyclization and purification are carried out as in Example 2. The purified peptide has the formula:

(cyclo)CbmTyr-D-Cys-Lys-Phe-Phe-D-Trp-IAmp-Thr-Phe-Thr-Ser-Cys-OH and is referred to as Peptide No. 14C. MS analysis shows a mass of 1691.6 Da which compares favorably with the calculated mass of 1690.73 Da.

EXAMPLE 15

The synthesis described in Example 9A is repeated but this time N$^α$Boc-Phe is used instead of N$^α$Boc-Tyr(2BrZ) for the 11-position to produce the 11-residue peptide. Cleavage, deprotection, cyclization, and purification are carried out as in Example 2. The purified cyclic peptide has the formula:

(cyclo)H-Cys-Lys-Phe-Phe-D-2Nal-N$^α$MeIAmp-Thr-Phe-Thr-Ser-Cys-OH and is referred to as Peptide No. 15. MS analysis shows a mass of 1510.8 Da, which compares favorably to the calculated value 1509.7.

EXAMPLE 16

The synthesis described in Example 9A is again repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 12 is carried out which results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo)CbmCys-Lys-Phe-Phe-D-2Nal-N$^α$MeIAmp-Thr-Tyr-Thr-Ser-Cys-OH and is referred to as Peptide No. 16. MS analysis shows a mass of 1569.6 Da, which compares favorably to the calculated value of 1568.7.

EXAMPLE 17

The synthesis described in Example 2 is repeated with one change. Following removal of the Boc group at the N-terminus, a reaction is carried out with an alkyl isocyanate to add a methyl carbamoyl moiety at the N-terminus.

After deblocking the α-amino group at the N-terminus using trifluoroacetic acid (TFA), a reaction is carried out with about 1 gm of the peptidoresin and 100 mg of methyl isocyanate in the presence of 2.7 mmol of DIEA for 2 hours at 22° C. in DMF (10 ml). This reaction results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo 3-14)MeCbm-Cys-Lys-Phe-Phe-D-Trp-N$^α$MeIAmp-Thr-Tyr-Thr-Ser-Cys-OH and is referred to as Peptide No. 17.

EXAMPLE 18

The synthesis described in Example 12 is repeated with one change. Following removal of the Boc group at the N-terminus, the reaction that is carried out to add a carbamoyl moiety employs a large (i.e. 6–7×) excess of NaOCN and thus creates a significant portion of the end product that has a biuret group at the N-terminus.

After deblocking the α-amino group at the N-terminus using trifluoroacetic acid (TFA), a reaction is carried out with about 1 gm of the peptidoresin about 650 mg of NaOCN and 5 ml of acetic acid for 30 min. at 22° C. in 10 ml of NMP. The reaction results in the addition of a carbamoyl moiety to the urea group that is initially formed at the N-terminus. Thereafter, cleavage of the peptide from the resin and deprotection of the side chain protecting groups, followed by cyclization and purification, are carried out as in Example 2. A substantial portion of the purified cyclic peptide has the formula:

(cyclo)Biucys-Lys-Phe-Phe-D-Trp-N$^α$MeIAmp-Thr-Tyr-Thr-Ser-Cys-OH and is referred to as Peptide No. 18.

Peptides 17 and 18 bind strongly and selectively to SSTR1.

EXAMPLE 19

The synthesis described in Example 9A is repeated with one change. N$^α$MeBoc-Ser(Bzl) is used to provide the 13-position residue. Further elongation of the chain then proceeds as in Example 15, and cleavage, deprotection, cyclization, and purification are carried out as in Example 2. The purified, cyclic peptide has the formula:

(cyclo)H-Cys-Lys-Phe-Phe-D-2Nal-N$^α$MeIAmp-Thr-Tyr-Thr-N$^α$MeSer-Cys-OH and is referred to as Peptide No. 19.

EXAMPLE 19A

The synthesis described in Example 19 is repeated with two changes. Boc-Phe is used to provide the 11-position residue, and Boc-IAmp(Z) is used to provide the 9-position residue. Cleavage, deprotection, cyclization, and purification are carried out as in Example 2. The purified, cyclic peptide has the formula:

(cyclo)H-Cys-Lys-Phe-Phe-D-2Nal-IAmp-Thr-Phe-Thr-N$^α$MeSer-Cys-OH and is referred to as Peptide No. 19A.

MS analysis shows a mass of 1510.5 Da, which compares favorably to the calculated value of 1510.69 Da.

EXAMPLE 20

The synthesis described in Example 2 is repeated, this time using N$^\alpha$MeBoc-Ser(Bzl) to provide the 13-position residue. Following removal of the Boc group, further elongation of the chain, as in Example 2 is carried out, followed by cleavage, deprotection, cyclization, and purification as in Example 2. The purified, cyclic peptide has the formula:

(cyclo)H-Cys-Lys-Phe-Phe-D-Trp-N$^\alpha$MeIAmp-Thr-Tyr-Thr-NMeSer-Cys-OH and is referred to as Peptide No. 20.

EXAMPLE 21

The synthesis described in Example 14 is repeated with one change. N$^\alpha$MeBoc-Ser(Bzl) is used for the 13-position residue. Elongation is then carried out as in Example 14, including a reaction to add a carbamoyl moiety and thus create a urea group at the N-terminus.

Thereafter, cleavage of the peptide from the resin and deprotection of the side chain protecting groups, followed by cyclization and purification, are carried out as in Example 2. The purified cyclic peptide has the formula:

(cyclo)CbmCys-Lys-Phe-Phe-D-Trp-N$^\alpha$MeIAmp-Thr-Tyr-Thr-N$^\alpha$MeSer-Cys-OH and is referred to as Peptide No. 21.

EXAMPLE 21A

The synthesis described in Example 21 is repeated with one change. Boc-IAmp(Z) is used for the 9-position residue. Elongation is then carried out as in Example 14, including a reaction to add a carbamoyl moiety and thus create a urea group at the N-terminus. Cleavage of the peptide from the resin and deprotection of the side chain protecting groups, followed by cyclization and purification, are carried out as in Example 2. The purified cyclic peptide has the formula:

(cyclo)CbmCys-Lys-Phe-Phe-D-Trp-IAmp-Thr-Tyr-Thr-N$^\alpha$MeSer-Cys-OH and is referred to as Peptide No. 21A.

Peptides 19 to 21A bind strongly and selectively to SSTR1.

EXAMPLE 22

The synthesis described in Example 13 is repeated with one change: N$^\alpha$MeBoc-Ser(Bzl) is used to provide the 13-position residue.

Cleavage, deprotection and cyclization are then carried out as in Example 2. The cyclized peptide is then purified by subjection to analytical HPLC on a C$_{18}$ column. The purified cyclic peptide has the formula:

(cyclo)H-Cys-Lys-Phe-Phe-D-Trp-N$^\alpha$MeIAmp-Thr-Phe-Thr-NMeSer-Cys-OH and is referred to as Peptide No. 22.

EXAMPLE 22A

The synthesis described in Example 22 is repeated with one change: Boc-IAmp(Z) is used to provide the 9-position residue. Cleavage, deprotection and cyclization are then carried out as in Example 2. The cyclized peptide is then purified by subjection to analytical HPLC on a C$_{18}$ column. The purified cyclic peptide has the formula:

(cyclo)H-Cys-Lys-Phe-Phe-D-Trp-IAmp-Thr-Phe-Thr-N$^\alpha$MeSer-Cys-OH and is referred to as Peptide No. 22A.

MS analysis shows a mass of 1499.8 Da, which compares favorably to the calculated value of 1498.68 Da.

EXAMPLE 23

The synthesis described in Example 22 is repeated with one change. N$^\alpha$Boc-D-Cys(Mob) is used instead of NBoc-Cys(Mob). Cleavage, deprotection, cyclization, and purification are carried out as in Example 2. The purified, cyclic peptide has the formula:

(cyclo)H-D-Cys-Lys-Phe-Phe-D-Trp-N$^\alpha$MeIAmp-Thr-Phe-Thr-N$^\alpha$MeSer-Cys-OH and is referred to as Peptide No. 23.

EXAMPLE 24

The synthesis described in Example 15 is repeated with one change. Following removal of the Boc group at the N-terminus, a reaction is carried out to add a carbamoyl moiety and thus create an urea group at the N-terminus.

After deblocking the α-amino group at the N-terminus using trifluoroacetic acid (TFA), a reaction as described in Example 12 is carried out and results in the addition of the carbamoyl moiety at the N-terminus. Thereafter, cleavage of the peptide from the resin and deprotection of the side chain protecting groups, followed by cyclization and purification, are carried out as in Example 2. The purified cyclic peptide has the formula:

(cyclo)CbmCys-Lys-Phe-Phe-D-2Nal-N$^\alpha$MeIAmp-Thr-Phe-Thr-Ser-Cys-OH and is referred to as Peptide No. 24.

Peptides Nos. 22 to 24 bind selectively and strongly to human SSTR1.

EXAMPLE 25

The synthesis described in Example 2 is repeated with one change. Following removal of the Boc group at the N-terminus, a reaction is carried out to add DOTA (1,4,7,10-tetraazacyclododecane N,N',N'',N'''-tetraacetic acid) and thus provide a polyaminopolycarboxylic chelant at the N-terminus. N-hydroxysuccinimide ester is prepared by modification of a procedure described by Lewis et al., *Bioconjugate Chem.* 5: 565–76 (1994). Freshly prepared EDC in H$_2$O (12.25 mg in 40 µl, 64 µmol) is added to a solution of 60 mg (128 µmol) of trisodium DOTA (Parish Chemicals) and 27.7 mg (128 µmol) of sulfo-NHS in 960 µL of H$_2$O at 4° C. The reaction mixture is stirred at 4° C. for 30 minutes. The theoretical concentration of active ester in the reaction mixture is 64 mM.

After deblocking the α-amino group at the N-terminus using trifluoroacetic acid (TFA), a reaction is carried out with the active ester solution at a pH of about 8.5. The mixture is stirred for 18 hours at 4° C. This reaction results in the addition of the DOTA moiety at the N-terminus. Thereafter, cleavage of the peptide from the resin and deprotection of the side chain protecting groups, followed by cyclization and purification, are carried out as in Example 2. The purified cyclic peptide has the formula:

(cyclo) (DOTA)Cys-Lys-Phe-Phe-D-Trp-N$^\alpha$MeIAmp-Thr-Tyr-Thr-Ser-Cys-OH and is referred to as Peptide No. 25.

EXAMPLE 26

The synthesis described in Example 25 is repeated with one change. The reaction at the N-terminus is carried out so as to add a different polyaminopolycarboxylic chelant moiety, namely DPTA (diaminetrimethylenepentaacetic acid). A solution of 40 g DTPA (0.102 mol) in 1.2 l of dry dimethylsulfoxide (DMSO) is prepared by heating and stirring, then it is cooled at room temperature and added with a solution of 11.73 g NHS (0.102 mol) in 300 ml DMSO, then, drop by drop, with a solution of 19.6 g of N,N'-dicyclohexylcarbodiimide (0.097 mol) in 400 ml DMSO. The mixture is stirred for 16 hours, then filtered, and the filtrate is concentrated by evaporation at 50° C. and 5 Pa to a thick oil of an about 160 ml volume.

After deblocking the α-amino group at the N-terminus using trifluoroacetic acid (TFA), a reaction is carried out with about 1 gm of the peptidoresin and the oil (added in portions) 0.1 M borate buffer pH 8, and 0.1 M NaCl, keeping pH at 8 by the simultaneous addition of 2 N NaOH. At the end of the additions, the mixture is stirred for 16 hours, then filtered and purified from by-products and excess reagents by chromatographic desalting on a Sephadex G-25 column. This reaction results in the addition of the DPTA moiety at the N-terminus. Thereafter, cleavage of the peptide from the resin and deprotection of the side chain protecting groups, followed by cyclization and purification, are carried out as in Example 2. The purified cyclic peptide has the formula:

(cyclo) (DPTA)Cys-Lys-Phe-Phe-D-Trp-N$^\alpha$MeIAmp-Thr-Tyr-Thr-Ser-Cys-OH and is referred to as Peptide No. 26.

Peptides 25 and 26 continue to bind strongly and selectively to SSTR1 despite the presence of the chelants at each N-terminus.

EXAMPLE 27

The synthesis described in Example 13 is repeated with one change. Elongation of the chain by one residue is carried out by coupling N$^\alpha$Boc-Tyr(2BrZ) at the N-terminus.

Cleavage, deprotection, cyclization and purification are carried out as in Example 2. The purified, cyclic peptide has the formula:

(cyclo)H-Tyr-Cys-Lys-Phe-Phe-D-Trp-N$^\alpha$MeIAmp-Thr-Phe-Thr-Ser-Cys-OH and is referred to as Peptide No. 27. This peptide and peptides which include Tyr$^{11}$ are readily radioiodinated with $^{125}$I to provide ligands for use in competitive drug screening assays. Following radioiodination, Peptide No. 27 continues to bind strongly to SSTR1 as did Peptide 2A.

In vitro Bioassay: The various somatostatin analogs are tested in vitro for their ability to bind to isolated cloned receptors expressed on CHO-K1 cells and CCL39 cells. CHO-K1 cells are grown in Ham's F-12 medium, and CCL39 cells are grown in Dulbecco's modified Eagle's medium/Ham's F-12(1:1) mix, supplemented with 10% fetal bovine serum, 100 U/ml penicillin and 100 μg/ml streptomycin, in humidified air containing 5% $CO_2$ at 37° C.

The molecular cloning of the genes encoding multiple somatostatin receptor subtypes permits the individual expression of these receptors in mammalian cells and the characterization of their respective pharmacological profiles. Five such receptor subtypes, termed SSTR1 through SSTR5, have been cloned and are reported and described in Raynor et al., *Molecular Pharmacology*, 43, 838–844 (1993) and in Raynor et al., *Molecular Pharmacology*, 44, 385–392 (1993). These references describe binding assays that can be used to determine whether particular SRIF analogs bind selectively to one or more of the 5 receptor types and also whether they bind to such receptor types with high or low affinity. Because these receptor types have now generally been characterized with regard to their pharmacological profiles, knowledge of the results of such binding studies, along with knowledge of the unique patterns of distribution of these receptors in the body indicate that each receptor subtype may mediate distinct but overlapping physiological effects of SRIF. As a result, compounds which bind selectively to receptors SSTR1, for example, can be used to modulate a particular physiological function of SRIF without potentially having an undesired effect resulting from another physiological function of SRIF which is mediated by other SRIF receptors.

Cells are washed and prepared to produce homogenates as described in detail in Reubi, J. C. et al, *Eur. J. Nucl. Med.* 2000, 27, 273–282.

Modulation of forskolin-stimulated adenylate cyclase activity was determined using a radioimmunoassay measuring intracellular cAMP levels by competition binding. SSTR1-expressing cells were subcultured in 96-well culture plates at $2\times10^4$ cells/well and grown for 24 hours. Culture medium was removed from the wells, and 100 μl of fresh medium containing 0.5 mM 3-isobutyl-I-methylxanthine (IBMX) were added to each well. Cells were incubated for 30 min. at 37° C. Medium was then removed and replaced with fresh medium containing 0.5 mM IBMX, with or without 3 μM forskolin and various concentrations of peptides. Cells were incubated for 30 min. at 37° C. After removal of medium, cells were lysed, and cAMP accumulation was determined using a commercially available cAMP scintillation proximity assay (SPA) system (RPA 538), according to the instructions of the manufacturer (Amersham, Aylesbury, UK). In these studies, basal levels of cAMP production were 0.25±0.02 μmol cAMP/well, rising to 3.2±0.2 pmol cAMP/well in the presence of 3 μM forskolin representing a 12.8±1.2 fold stimulation.

cAMP data are expressed as percentage of stimulation over the non-stimulated level. Values of $EC_{50}$ (the agonist concentration causing 50% of its maximal effect) are derived from concentration-response curves.

Receptor autoradiography is performed on 20 μm thick cryostat sections of the membrane pellets, mounted on microscope slides, and then stored at −20° C. For each of the tested compounds, complete displacement experiments are performed with the universal somatostatin ligand radioligand $^{125}$I -[Leu$^8$,D-Trp$^{22}$,Tyr$^{25}$]-somatostatin-28 that binds with strong affinity to all five receptors. Increasing concentrations of the unlabeled peptide are used ranging from 0.1–1000 nM. Unlabeled somatostatin-28 is run in parallel using the same increasing concentrations, as a control. $IC_{50}$ values are calculated after quantification of the data using a computer-assisted image processing system as known in this art. At concentrations of 100 nM, Peptide No. 2 had minimal effects on the binding of the SRIF-28 radioligand to human SSTR2, SSTR3, SSTR4 and SSTR5 and Peptides 2A and 2B have even less effect. In contrast, Peptide No. 2 is selectively bound to SSTR1, displacing the binding of the radioligand to human SSTR1 with an $IC_{50}$ value of about 6.1 nM, and Peptides Nos. 2B and 2A showed binding affinities of 3.6 and 17.1 nM respectively. Peptide No. 12 with the urea group at the N-terminus shows good selectivity with good binding strength, and Peptides Nos. 12B and 12A also show strong binding affinities of 2.5 and 8.1 nM respectively. Peptide No. 9A containing the D-2Nal$^8$ modification selectively binds to SSTR1 and exhibits an $IC_{50}$ of about 21 nM. Peptide No. 15, the analog with the D-2Nal$^8$ modification and with Phe$^{11}$, also selectively binds to SSTR1, exhibiting an $IC_{50}$ of about 32.5. The addition of a carbamoyl to the N-terminus of Peptide 9A produces Peptide 16 having an $IC_{50}$ of about 32, whereas the carbamoyl addition to a peptide-extended with Tyr at the N-terminus shows a high binding affinity of 15 in an analog (No. 14A) that can be radioiodinated while remaining SSTR1-selective. Peptide No. 13 with D-Trp$^8$ modification and with Phe$^{11}$ likewise selectively binds SSTR1; it exhibits an IC$_{50}$ of about 8.7 nM.

To confirm that an iodinated version of one of these analogs may serve as a selective SSTR1 radioligand, Peptide No. 27, i.e. the N-terminus-extended Tyr$^2$ analog of Peptide No. 13, is synthesized, iodinated and tested for binding to the five cloned SRIF receptors. No specific binding of Peptide No. 27 to SSTR2, 3, 4 and 5 is detectable. In contrast, Peptide No. 27 effectively binds to SSTR1 to about the same extent as Peptide No. 13. Moreover, it is believed that its binding strength and/or selectivity can be improved by acylation of the Tyr (with its phenolic hydroxyl protected) with carbamoyl (see Peptide No. 14B) or that the alternative substitution and iodination of an analog containing Tyr$^{11}$ (see Peptide No. 2B) may provide improved binding compared to the comparable Tyr$^2$ analog.

Screening assays, as are well known in the art which employ the receptor polypeptide SSTR1 directly from the recombinant host, can be used to identify agents useful in blocking or mimicking certain aspects of somatostatin as desired while eliminating the undesirable aspects of the hormone which may arise from activation or blocking of other receptors.

The potencies of certain SRIF analogs to inhibit radioligand binding of $^{125}$I-[Leu$^8$,D-Trp$^{22}$,Tyr$^{24}$]SRIF-28 to the various cloned SRIF receptors are shown in the following table wherein the IC$_{50}$ values are given in nanomolar concentration.

TABLE

| Compound | IC$_{50}$ (nM) | | | | |
|---|---|---|---|---|---|
| | mSSTR1 | mSSTR2 | mSSTR3 | mSSTR4 | mSSTR5 |
| Peptide No. 2 | 7.2 | >10,000 | >1,000 | >1,000 | >10,000 |
| Peptide No. 2A | 17.1 | >10,000 | >1,000 | >10,000 | >1,000 |
| Peptide No. 2B | 3.6 | >10,000 | >1,000 | >1,000 | >1,000 |
| Peptide No. 5A | 35 | >1,000 | 975 | >1,000 | >1,000 |
| Peptide No. 9A | 24.5 | >10,000 | >1,000 | >1,000 | >10,000 |
| Peptide No. 12 | 43 | >10,000 | >1,000 | >1,000 | >10,000 |
| Peptide No. 12A | 8.1 | >10,000 | >1,000 | >1,000 | >1,000 |
| Peptide No. 12B | 2.5 | >10,000 | 618 | >1,000 | >1,000 |
| Peptide No. 12C | 17.4 | >10,000 | >1,000 | >10,000 | >1,000 |
| Peptide No. 12D | 8.5 | >1,000 | >1,000 | 700 | >1,000 |
| Peptide No. 13 | 8.7 | >10,000 | 610 | 200 | >10,000 |
| Peptide No. 14A | 15 | >10,000 | 500 | >1,000 | >1,000 |
| Peptide No. 14B | 34.7 | >1,000 | 290 | >1,000 | >1,000 |
| Peptide No. 14C | 33 | >10,000 | >1,000 | 487 | >1,000 |
| Peptide No. 15 | 43 | >1,000 | >1,000 | >1,000 | >10,000 |
| Peptide No. 16 | 32 | >10,000 | >1,000 | >10,000 | >10,000 |
| Peptide No. 22A | 25 | >10,000 | 600 | >1,000 | >1,000 |

TABLE-continued

| Compound | IC$_{50}$ (nM) | | | | |
|---|---|---|---|---|---|
| | mSSTR1 | mSSTR2 | mSSTR3 | mSSTR4 | mSSTR5 |
| Peptide No. 27 | 25 | >10,000 | >1,000 | 300 | >10,000 |

The peptides of the invention not only provide more selective ligands for binding SSTR1 but the use of labeled peptides, for example, a radioiodinated version of one of Peptide Nos. 2B, 12B, 12D, 14B or 27, facilitates drug screening for even more effective antagonists. Competitive binding assays with candidate compounds would first be carried out in this manner with SSTR1 to search for high binding affinity; then by screening the multiple SRIF receptors, it could be confirmed whether there was selective binding to only this receptor, as is desired.

Because, as shown above, additions to the N-terminus of the SRIF analog do not appear to adversely affect the selective binding, it should be clear that these compounds can be complexed with a cytotoxic or a radioactive agent for the purpose of carrying that agent to a tumor or other tissue for which degradation is desired. For example, a dialdehyde linker such as glutaraldehyde may be used to link the SRIF analog to saporin or gelonin. Likewise, linkers such as DOTA or DTPA or other suitable chelating agents can be used to complex the SRIF analog with a highly radioactive element as indicated hereinbefore. If desired, the solubility of the SRIF analogs can be improved by acylation of the N-terminal amino group using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the SRIF analog as known in this art.

These SRIF analogs or nontoxic salts thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician to combat specific tumors and cancers or to mediate other conditions where the SSTR3 receptors exert a control function, such as coupling to a tyrosine phosphatase so that stimulation of this enzyme can be carried out to mediate the anti-proliferative effects of SRIF. The required dosage will vary with the particular condition being treated, with the severity of the condition and with the duration of desired treatment.

Such peptides are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver these SRIF analogs over prolonged periods of time, for example, for periods of one week to one year from a single administration, and slow release, depot or implant dosage forms may be utilized as well known in this art. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain an SRIF analog or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptides should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of an SRIF analog that, when administered peripherally, e.g. intravenously, in a physiologically acceptable composition, is sufficient to achieve a plasma concentration thereof from about 0.1 µg/ml to about 100 µg/ml, preferably from about 1 µg/ml to about 50 µg/ml, more preferably at least about 2 µg/ml and usually 5 to 10 µg/ml. In these amounts, they may be used for the prevention of IH, or in appropriate treatments for cardiovascular diseases and other SSTR1-mediated physiopathologies.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. Although the claims variously define the invention in terms of a peptide sequence, it should be understood that such is intended to include nontoxic salts thereof which are well known to be the full equivalent thereof and which are most frequently administered. Instead of the simple free acid at the C-terminus, a lower alkyl ester or amide may be incorporated as well known in the peptide art. Cyclic peptides having an amino acid residue sequence substantially identical to the sequence of the SRIF analogs specifically shown herein, in which one or more residues have been conservatively substituted with a functionally similar amino acid residue, are considered to be equivalents so long as they selectively bind to SSTR1.

As previously indicated, these specified modifications can be incorporated in previously disclosed SRIF analogs to create SSTR1-selectivity. The inclusion of residues in the 1- and 2-positions is optional, but except for Tyr, D-Tyr or D-Ala, such elongation is not considered worthwhile unless it would favorably influence solubility and/or resistance to aminopeptidases. Often a carbamoyl moiety or a conjugating agent will be linked to the α-amino group of the residue at the N-terminus of these peptides, and these moieties are included in the definition of $Xaa_1$. Broadly it is considered that cyclic somatostatin analog peptides having specific high affinity for the SRIF receptor SSTR1 can be created by modifying the amino acid sequence of existing SRIF analogs which are known in the art to exhibit SRIF biological activity. The modified peptide should contain a Cys-Cys disulfide bond with a sequence of at least 9 residues located between such Cys residues as a ring structure with the 5-position residue being deleted; it should contain Lys-Phe-Phe-D-$Xaa^8$-$N^\alpha$MeIAmp-Thr-Tyr or its equivalent adjacent the N-terminal Cys of the ring structure. Such cyclic SRIF analogs may also be modified by N-methylation of the α-amino group on another residue in the ring sequence to create resulting SRIF analogs that retain their high specificity for SSTR1. Such peptides and salts thereof are considered as being within the scope of the claimed invention. The inclusion of a carbamoyl moiety or a lower alkyl carbamoyl, preferably methyl, ethyl or isopropyl, or biuret at the N-terminus of any of these analogs should not detract from selectivity and is expected to increase the duration of biological activity following administration.

As used herein, all temperatures are ° C. and all ratios are by volume. Percentages of liquid materials are also by volume. The disclosures of all U.S. patents and patent applications and publications set forth hereinbefore are expressly incorporated by reference.

Various features of the invention are emphasized in the claims which follow.

What is claimed is:

1. A cyclic somatostatin (SRIF) analog peptide which selectively binds SRIF receptor SSTR1, which peptide has the amino acid sequence (cyclo 3-14) $X_1$-$X_2$-$X_3$-Lys-Phe-$X_7$-$X_8$-$X_9$-Thr-$X_{11}$-Thr-$X_{13}$-Cys wherein:
   $X_1$ is des-$X_1$, Ala, D-Ala, Cbm, Biu, (lower alkyl)Cbm, L-Hor, an acyl group having up to 20 carbon atoms, lower alkyl or a conjugating/complexing agent;
   $X_2$ is Tyr, ITyr, D-Tyr, D-ITyr, Gly, or des-$X_2$;
   $X_3$ is Cys or D-Cys;
   $X_7$ is (A)Phe wherein A is H, Cl, F, Br, $NO_2$, Me, or NH(Q), where Q is H, Cbm, or L-Hor;
   $X_8$ is a D-isomer amino acid having an aromatic side chain;
   $X_9$ is an aminomethyl Phe wherein the side chain is ($C_2$ to $C_5$)alkylated and which is $N^\alpha$methylated;
   $X_{11}$ is Phe, Tyr or ITyr; and
   $X_{13}$ is Ser, $N^\alpha$MeSer or D-Ser.

2. The peptide according to claim 1 wherein:
   $X_1$ is des-$X_1$, D-Ala, Ala, Cbm, Biu, L-Hor or an acyl group having up to 7 carbon atoms;
   $X_2$ is Tyr, ITyr, D-Tyr, D-ITyr or des-$X_2$;
   $X_3$ is Cys or D-Cys;
   $X_7$ is (A)Phe wherein A is H, 4Cl, 4F or $NO_2$;
   $X_8$ is a D-isomer amino acid having an aromatic side chain; and
   $X_9$ is IAmp.

3. The peptide according to claim 2 wherein $X_8$ is D-Trp.

4. The peptide according to claim 2 wherein $X_8$ is D-2Nal.

5. The peptide according to claim 2 wherein $X_1$ is des-$X_1$, $X_2$ is des-$X_2$ and $X_{11}$ is Tyr or ITyr.

6. The peptide according to claim 1 wherein $X_1$ is a conjugating/complexing agent capable of linking to a cytotoxin or complexing to a radioactive nuclide.

7. The peptide according to claim 6 wherein $X_8$ is D-Trp or D-2Nal and $X_{11}$ is Tyr.

8. The peptide according to claim 6 wherein $X_1$ is a polyaminopolycarboxylic conjugating agent.

9. The peptide of according to claim 6 wherein said conjugating/complexing agent is DOTA, DTPA, HYNIC or $P_2S_2$-COOH.

10. The peptide according to claim 1 having the amino acid sequence: (cyclo 3-14) $X_1$-$X_2$-$X_3$-Lys-Phe-$X_7$-$X_8$-N$^\alpha$MeIAmp-Thr-$X_{11}$-Thr-$X_{13}$-Cys wherein:
   $X_1$ is Cbm;
   $X_2$ is des-$X_2$;
   $X_8$ is D-Trp or D-2Nal; and
   $X_{11}$ is Tyr or ITyr.

11. The peptide according to claim 1 having the amino acid sequence: (cyclo 3-14) $X_1$-Cys-Lys-Phe-$X_7$-$X_8$-N$^\alpha$MeIAmp-Thr-$X_{11}$-Thr-$X_{13}$-Cys wherein:
   $X_1$ is Cbm or des-$X_1$;
   $X_7$ is Phe or 4NO$_2$Phe; and
   $X_{11}$ is Tyr or ITyr.

12. A pharmaceutical composition comprising a mixture of the peptide according to claim 1 and at least one phamaceutically acceptable carrier.

13. A cyclic somatostatin (SRIF) analog peptide having the amino acid sequence: (cyclo 3-14) $X_1$-$X_2$-$X_3$-Lys-Phe-Phe-D-Trp-N$^\alpha$MeIAmp-Thr-$X_{11}$-Thr-Ser-Cys wherein:
   $X_1$ is Cbm or des-$X_1$;
   $X_2$ is Tyr, ITyr, D-Tyr, D-ITyr or des-$X_2$;
   $X_3$ is Cys or D-Cys; and
   $X_{11}$ is Phe, Tyr or ITyr.

14. The peptide of claim 13, wherein $X_{11}$ is Tyr or ITyr and I is radioactive.

15. The peptige according to claim 13 having the amino acid sequence:
   (cyclo 3-14)H-Cys-Lys-Phe-Phe-D-Trp-N$^\alpha$MeIAmp-Thr-Tyr-Thr-Ser-Cys-OH.

16. A cyclic somatostatin (SRIF) analog peptide which selectively binds the SRIF receptor SSTR1, which peptide has the amino acid sequence (cyclo 3-14) $X_1$-$X_2$-$X_3$-Lys-Phe-Phe-D-Trp-$X_9$-Thr-$X_{11}$-Thr-Ser-Cys wherein:
   $X_1$ is des-$X_1$, Ala, D-Ala, Cbm, Biu, (lower alkyl)Cbm, L-Hor, an acyl group having up to 20 carbon atoms, lower alkyl or a conjugating/complexing agent;
   $X_2$ is Tyr, ITyr, D-Tyr, D-ITyr, Gly, or des-$X_2$;
   $X_3$ is Cys or D-Cys;
   $X_9$ is an aminomethyl Phe which is N$^\alpha$methyated and has a side chain that is ($C_2$ to $C_5$)alkylated;
   $X_{11}$ is Phe, Tyr, D-Tyr, ITyr or D-ITyr; and
   $X_{13}$ is Ser, N$^\alpha$MeSer or D-Ser.

17. The peptide according to claim 16 wherein:
   $X_1$ is Cbm, Biu, (lower alkyl)Cbm or des-$X_1$;
   $X_2$ is des-$X_2$; and
   $X_{11}$ is Tyr or ITyr.

18. The peptide according to claim 16 wherein $X_1$ is Cbm and $X_9$ is N$^\alpha$MeIAmp.

19. The peptide according to claim 16 wherein $X_{13}$ is is N$^\alpha$MeSer.

20. The peptide according to claim 1 having the amino acid sequence: (cyclo 3-14) $X_1$-Cys-Lys-Phe-$X_7$-D-Trp-N$^\alpha$MeIAmp-Thr-$X_{11}$-Thr-$X_{13}$-Cys wherein:
   $X_1$ is Cbm or des-$X_1$;
   $X_7$ is Phe or 4NO$_2$Phe;
   $X_{11}$ is Tyr or ITyr; and
   $X_{13}$ is Ser or N$^\alpha$MeSer.

* * * * *